(12) United States Patent
Brown et al.

(10) Patent No.: US 10,487,971 B2
(45) Date of Patent: Nov. 26, 2019

(54) WELDLESS SAMPLE PORT

(71) Applicant: REM Technology Inc., Calgary (CA)

(72) Inventors: Gregory Anthony Brown, Calgary (CA); Brian Bobyk, Calgary (CA)

(73) Assignee: REM TECHNOLOGY INC., Calgary (CA)

( * ) Notice: Subject to any disclaimer, the term of this patent is extended or adjusted under 35 U.S.C. 154(b) by 106 days.

(21) Appl. No.: 15/612,372

(22) Filed: Jun. 2, 2017

(65) Prior Publication Data
US 2018/0347740 A1 Dec. 6, 2018

(51) Int. Cl.
*G01N 1/22* (2006.01)
*F16L 41/00* (2006.01)

(52) U.S. Cl.
CPC .......... *F16L 41/008* (2013.01); *G01N 1/2258* (2013.01)

(58) Field of Classification Search
CPC ...... G01N 1/02; G01N 1/10; G01N 2001/105; G01N 1/20; G01N 1/2035; G01N 1/22; G01N 1/2247; G01N 2001/225; G01N 2001/2258; G01N 201/1031; G01N 1/2258; F16L 41/008; F16L 41/12
USPC ............... 73/863.51, 863.81, 863.85, 864.73
See application file for complete search history.

(56) References Cited

U.S. PATENT DOCUMENTS

| | | | | |
|---|---|---|---|---|
| 3,217,546 A | * | 11/1965 | Cordell | G01N 1/20 73/863.56 |
| 5,309,773 A | * | 5/1994 | Tokoyama | B04C 5/13 209/576 |
| 2007/0251334 A1 | * | 11/2007 | Akers, Jr. | G01N 1/2035 73/863.71 |

* cited by examiner

*Primary Examiner* — Robert R Raevis
(74) *Attorney, Agent, or Firm* — Thompson Hine LLP

(57) ABSTRACT

A weldless sample port assembly is provided herein that may be installed on a conduit carrying a fluid such as an exhaust stack, without a requirement for welding. The sample port assembly comprises a sample tube that passes through two holes in the exhaust stack. The sample port assembly further comprises first and second assemblies located at each end of the sample tube and which respectively provide a sealed interface with the two holes in the exhaust stack. At least one assembly of the first and second assemblies is a floating assembly that comprises a compressive body. The compressive body may help to compensate for expansion and contraction of the assembly and/or sample tube, as well as misalignment in the exhaust holes to ensure that the first and second assemblies maintain a positive seal at all times against the exhaust stack and the sample tube.

17 Claims, 18 Drawing Sheets

WELDLESS SAMPLE PORT

TECHNICAL FIELD

The present disclosure relates to sample ports, and in particular to a weldless sample port for extracting a sample from a fluid contained in a conduit, such as a pipe, stack or cylinder.

BACKGROUND

In many combustion processes, components of exhaust emissions are monitored to ensure optimum equipment performance or regulatory compliance. Monitoring of the exhaust emissions is generally performed via one or more exhaust sample ports located on the periphery of an exhaust stack to extract a sample from the exhaust stack which can then be analyzed using chemical, optical or some other means to determine the constituents of the exhaust emissions.

FIG. 1 shows an industrial engine 50 connected to an exhaust stack 52 with a prior art sample port 54 installed thereon. The engine 50 reacts fuel and oxidizer in a combustion process and expels the combustion gases into the exhaust stack 52, which in turn directs the combustion gases to the atmosphere. To facilitate emissions measurement, a sample port 54 must often be retrofitted to the existing exhaust system at the combustion equipment's point of use (i.e. in the field).

FIG. 2 shows a detailed cross-sectional view of the prior art sample port 54 installed on the engine exhaust stack 52. The installation of the sample port 54 typically involves welding a pipe, tube or weld-o-let to the periphery of the exhaust stack 52 at joint 56, for example. A cap 58 may be placed at one end of the sample port 54 to prevent exhaust gases from venting to the atmosphere when the sample port is not in use.

Due to the presence of an open flame and the possibility of sparks occurring during the welding process, many industrial locations prohibit welding in hazardous locations unless strict safety regulations and procedures are adhered to. The need for a welder combined with the additional safety requirements when welding in hazardous locations results in additional costs and production losses to the end user. Further, due to high temperatures of the exhaust surface and combustion gas, as well as significant mechanical vibration, adhesive attachment of sample ports to the exhaust stack is typically unacceptable.

Accordingly, an additional, alternative, or improved sample port remains highly desirable.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
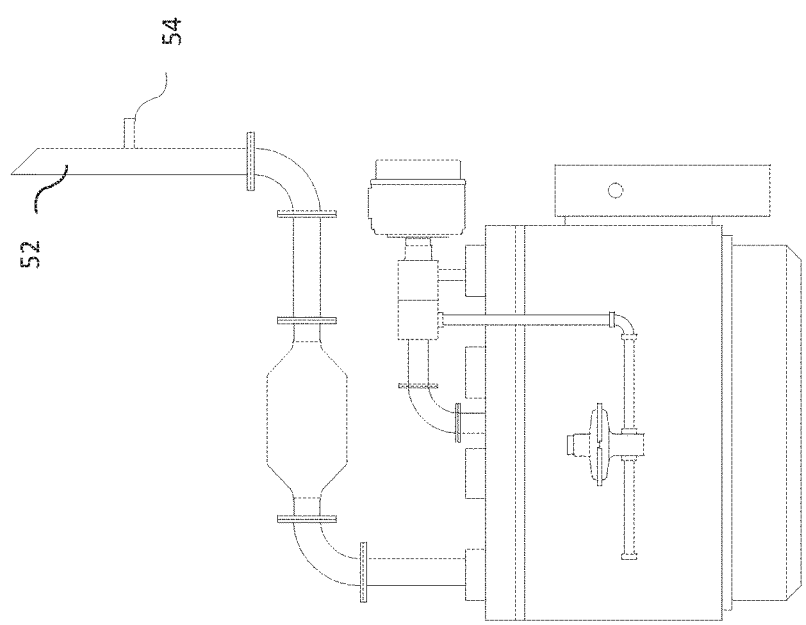
FIG. 1 shows an engine with a prior art sample port installed on its exhaust stack.
Figure 2:
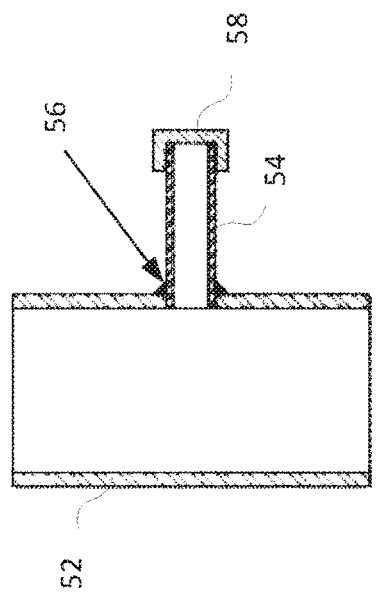
FIG. 2 shows a detailed cross-sectional view of the prior art sample port installed on the engine exhaust stack.

A weldless sample port assembly is provided herein that is, as an example, suitable for use with combustion type equipment to facilitate the measurement of exhaust emissions. The sample port assembly may be installed on a conduit carrying a fluid, such as an exhaust stack, without a requirement for welding. The sample port assembly comprises a sample tube of circular or non-circular cross-section that passes through two holes in the exhaust stack, where the two holes may be pre-existing or created at the time of installation perpendicular to the flow in the stack. The sample tube (or pipe) contains one or more holes or slots along the outer surface of the tube and located in the exhaust stream for receiving exhaust gas samples.

In one embodiment of the present disclosure there is provided a weldless sample port assembly for extracting a sample from a fluid carried by a conduit, the weldless sample port comprising: a sample tube inserted through two holes in the conduit, the sample tube arranged perpendicular to a direction of fluid flow and configured to receive a sample of fluid; a first assembly coupled to the sample tube at a first end of the sample tube outside of the conduit, the first assembly providing a compressively sealed interface with a first hole of the two holes in the conduit; and a second assembly coupled to the sample tube at a second end of the sample tube outside of the conduit, the second assembly providing a compressively sealed interface with a second hole of the two holes in the conduit.

The weldless sample port assembly may have at least one of the first assembly and the second assembly comprising a compressive body. The compressive body can have a pre-set compressive load stored therein. The first assembly can comprise the compressive body and can be a floating assembly, and the second assembly is a fixed assembly. The compressive body can comprise any one or more of a helical spring, a disc spring, a bi-metallic spring, a bushing, a bellow, and a diaphragm. The floating assembly can comprises a packing gland assembly, the compressive body comprises one of the helical spring, the disc spring, and the bi-metallic spring, and the compressive body is circumferentially wrapped around an external surface of the packing gland assembly. Each of the floating assembly and the fixed assembly can comprise a first sealing structure providing a first seal between the respective floating assembly and fixed assembly and the respective first hole and second hole, and a second sealing structure providing a second seal between the respective floating assembly and fixed assembly and the sample tube. 5 The first sealing structure of the floating assembly can comprise any one or more of: packing, a concave packing gland, a tapered packing gland, a threaded packing gland, a flat packing gland, and a packing gland with a saddle profile.

In an embodiment the second sealing structure of the floating assembly can comprise a packing. The first sealing structure of the fixed assembly can comprise any one or more of: a ferrule, packing, a concave packing gland, a tapered packing gland, a threaded packing gland, a flat packing gland, and a packing gland with a saddle profile. The second sealing structure of the fixed assembly can comprise any one or more of: a ferrule, and packing.

In an embodiment the first assembly and the second assembly may comprise respective compressive bodies and are both floating assemblies. The respective compressive bodies may comprise any one or more of a helical spring, a disc spring, a bi-metallic spring, a bushing, a bellow, and a diaphragm. At least one of the floating assemblies may further comprise a packing gland assembly, the compressive body comprises one of the helical spring, the disc spring, and the bi-metallic spring, and the compressive body is circumferentially wrapped around an external surface of the packing gland assembly. Each of the floating assemblies may comprise a first sealing structure providing a first seal between the respective floating assembly and the respective first hole and second hole, and a second sealing structure providing a second seal between the respective floating assembly and the sample tube. The first sealing structure may comprise any one or more of: packing, a concave packing gland, a tapered packing gland, a threaded packing gland, a flat packing gland, and a packing gland with a saddle profile. The second sealing structure comprises packing.

The weldless sample port may further comprise a first fitting and a second fitting interfacing with respective of the first assembly and the second assembly at a distal end thereof with respect to the conduit, the first and second fittings configured to be secured with the sample tube. The first fitting and second fitting may be configured to receive one or more of a sample measurement device and a cap.

The sample tube may comprises one of: a hole, a plurality of holes, or a slot, configured to receive the sample of fluid there through. The sample tube may be configured to receive a sample probe inserted there through, the sample probe comprising a sample probe tube and a sample probe hole at an end thereof for receiving the sample of fluid.

Another embodiment of the present disclosure is a method for installing a sample port assembly, comprising: inserting a sample tube through two holes in a conduit, the sample tube arranged perpendicular to a direction of fluid flow and configured to receive a sample of fluid; arranging a first assembly and a second assembly at respective ends of the sample tube outside of the conduit, at least one of the first assembly and the second assembly comprising a compressive body; securing a first fitting to the sample tube, the first fitting interfacing with the first assembly at a distal end of the first assembly with reference to the conduit; applying a compressive force to the first assembly and the second assembly; and once a pre-set load is achieved in the compressive body, securing a second fitting to the sample tube, the second fitting interfacing with the second assembly at a distal end of the second assembly with reference to the conduit.

The sample tube may be further configured to receive a sample probe inserted there through, the sample probe comprising a sample probe tube and a sample probe hole at an end thereof for receiving the sample of fluid, the method further comprising: inserting the sample probe into the sample tube through one of the first fitting or the second fitting and the respective first assembly or second assembly; aligning the sample probe hole to be configured to receive the sample of fluid from the one of the hole, a hole of the plurality of holes, or the slot in the sample tube; and securing the corresponding first or second fittings through which the sample probe was inserted there through to the sample probe tube.

Other aspects and features will become apparent to those ordinarily skilled in the art upon review of the following description of specific embodiments of the disclosure in conjunction with the accompanying figures.

The sample port assembly further comprises first and second assemblies located at each end of the sample tube and which respectively provide a sealed interface with the two holes in the exhaust stack. The first and second assemblies also provide a seal with the sample tube and exhaust stack to ensure that no exhaust gas escapes to the atmosphere and that no atmospheric gas enters the stack. Fittings may be coupled with the sample tube to secure the respective first and second assemblies against the exhaust stack. At least one assembly of the first and second assemblies is a floating assembly that comprises a compressive body. The compressive body may help to compensate for expansion and contraction of the assembly and/or sample tube, as well as misalignment in the exhaust holes to ensure that the first and second assemblies maintain a positive seal at all times against the exhaust stack and the sample tube.

The sample port design provides for standard process connections at each end of the sample tube to facilitate connections to sampling equipment. The sample port assembly may further provide accurate and consistent sample positioning, standardization of sample port configuration between combustion equipment of similar design, as well as support a wide range of conduit or exhaust stack sizes and configurations. The sampling of the fluid may be a liquid fluid or gaseous fluid sample.

While reference of the sample port assembly may be made to a potential use with combustion equipment, a person skilled in the art will readily appreciate that the teachings herein may be extended to various kinds of applications without departing from the scope of the invention. Such applications may include any fluid sampling or measurement from any conduit where a weldless solution may be required or would be beneficial, including but not limited to sampling or measurement of fluids in a hazardous or restricted location. In the description the exhaust stack provides the conduit transporting the exhaust gas fluid. It should be understood that the use of the weldless port is possible with any rigid or semi-rigid conduit which a sample port can be affixed.

While reference to the sample port assembly may be made to having a single sample port assembly installed on an exhaust stack, a person skilled in the art will readily appreciate that an exhaust stack may have more than one sample port and that the teachings herein may be applied to such a configuration accordingly.

Embodiments are described below, by way of example only, with reference to FIGS. 3-18.

Figure 3:
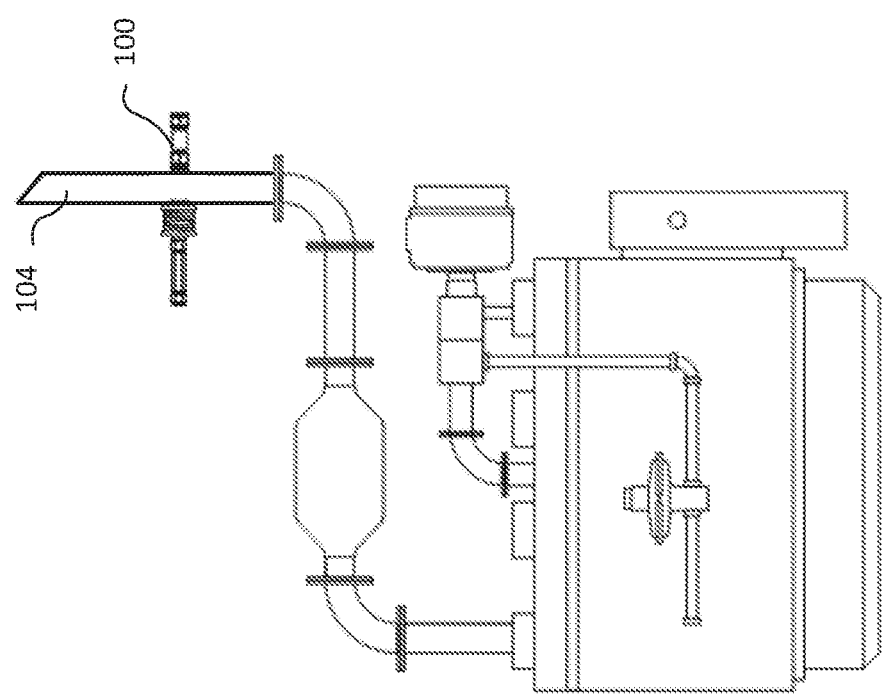
FIG. 3 shows an engine with a sample port assembly installed on its exhaust stack in accordance with the teachings herein.

FIG. 3 shows an engine 102 with a sample port assembly 100 in accordance with the teachings herein installed on its exhaust stack 104. As the sample port assembly 100 may typically be installed as a retrofit to the engine 102 in the field, the engine 102 may be the same or different than the engine 50 shown in FIG. 1.

Figure 4:
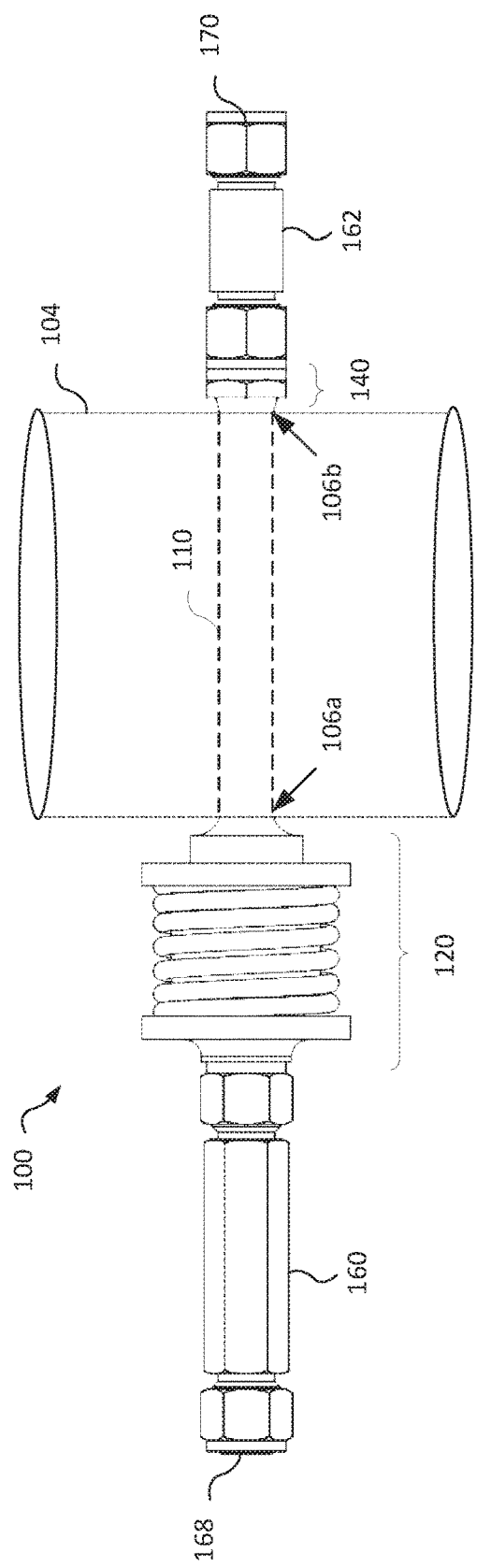
FIG. 4 shows a detailed view of the sample port assembly installed on the exhaust stack.

FIG. 4 shows a detailed view of the sample port assembly 100 installed on the engine exhaust stack 104. The sample port assembly 100 may comprise a sample tube 110 for receiving a sample from the fluid stream, and the sample tube 110 may traverse through the exhaust stack 104 substantially perpendicular to the direction of fluid flow. In particular, the sample tube 110 may pass through two exhaust through-holes 106a and 106b made in the surface of the exhaust stack 104. The exhaust stack 104 may be of circular, square, rectangular, or various other cross-sectional shapes. The two exhaust through-holes 106a and 106b may be substantially longitudinally- and vertically-aligned such that the sample tube 110 may pass through the exhaust stack 104 orthogonally to the two exhaust through-holes 106a and 106b.

The sample port assembly 100 further comprises first and second assemblies that interface with the respective exhaust through-holes 106a and 106b. The assemblies are shown in FIG. 4 as comprising a floating assembly 120 and a fixed assembly 140. The first and second assemblies may be the same or different as will be further described herein, but at least one of the first and second assemblies is a floating assembly 120. The floating assembly 120 and fixed assembly 140 are further described with reference to FIGS. 5 thru 11.

On the distal end of the respective floating assembly 120 and fixed assembly 140 with reference to the exhaust stack 104, the sample port assembly 100 may further comprise fittings 160 and 162 that may be used to help secure the assemblies against the exhaust stack 104 and provide a pressure-tight connection against the sample tube 110 for sample collection. The fittings 160 and 162 may include, but not be limited to: swaged fittings, threaded fittings, tapered fittings, compression fittings, flared fittings, and/or custom fittings. The fittings 160 and 162 may be secured to the sample tube 110 by tightening an inner nut of the fitting, for example. The fittings 160 and 162 may be bored-through for receiving the sample probe as will further be described with reference to FIG. 15.

The relative position of the fittings 160 and 162 away from the hot exhaust gases may reduce the likelihood of assembly components seizing due to material deformation and corrosion. The fittings 160 and 162 may be the same or different depending on the application and installation requirements, though in FIG. 4 the fittings 160 and 162 are shown as being slightly different. The fittings 160 and 162 may further provide a standard connection for connecting to sampling equipment (not shown in FIG. 4). When the sample port assembly 100 or a specific fitting is not in use, the fittings 160 and 162 may be sealed with a cap 168 and 170 respectively to prevent exhaust gases from escaping to the atmosphere.

Figure 5:
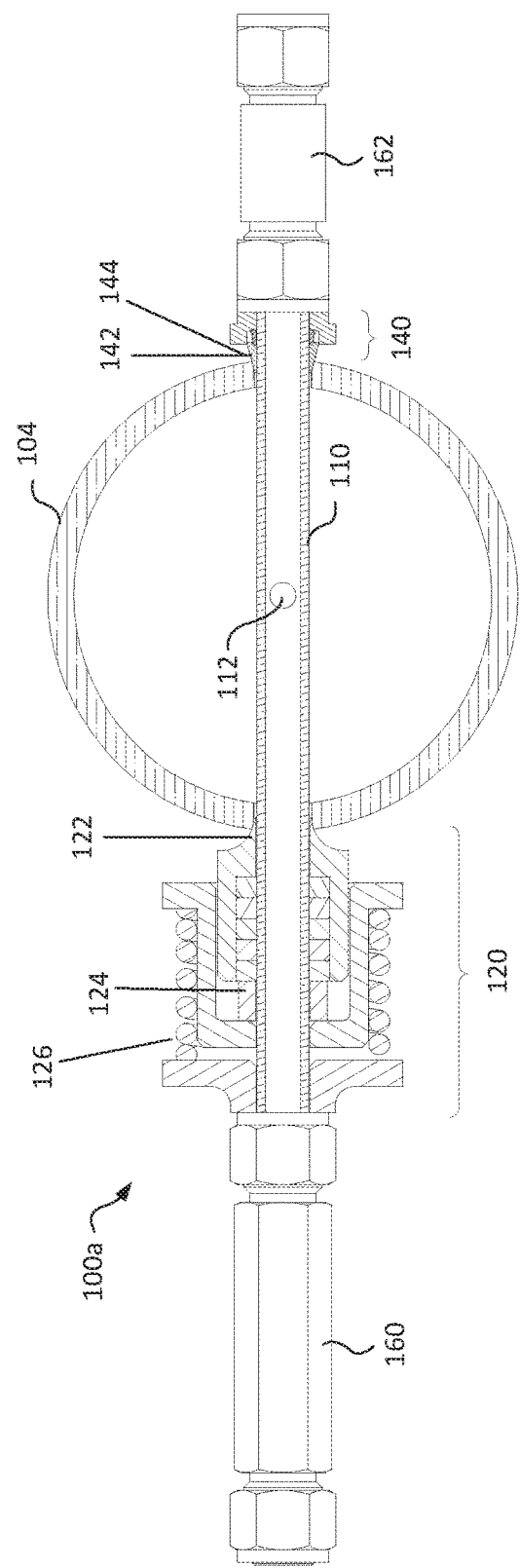
FIG. 5 shows a cross-sectional plan view of the sample port assembly installed on the exhaust stack.

FIG. 5 shows a cross-sectional plan view of the sample port assembly 100 installed on the exhaust stack 104. The sample port assembly 100a corresponds to a sample port configuration of having one floating assembly 120 and one fixed assembly 140. The sample tube 110 may comprise a sample hole 112 on an outer surface thereof for receiving a sample of the exhaust gas or other fluid. The orientation of the sample hole 112 may be perpendicular to the direction of fluid flow, though is not limited to such. For example, the sample hole 112 may be arranged parallel to the direction of fluid flow or at any angle relative to the direction of fluid flow. The floating assembly 120 may be able to compensate for expansion and contraction of the exhaust stack 104 and/or sample tube 110, as well as misalignment in the two exhaust through-holes 106a and 106b. This may help to ensure that the floating and fixed assemblies maintain a positive seal at all times against the exhaust through-holes 106a and 106b, as well as the sample tube 110. The fixed assembly 140 may be static and may not be able to compensate for expansion and contraction of the exhaust stack 104 and/or misalignment in the two exhaust through-holes 106a and 106b.

The floating assembly 120 and the fixed assembly 140 may each have a first sealing structure 122 and 142 providing a first seal for interfacing with the respective exhaust through-holes 106a and 106b. The first sealing structure 122 and 142 may help to ensure that exhaust gas does not leak to the atmosphere through the exhaust through-holes 106a and 106b and that atmospheric gas does not enter the exhaust stack 104. The floating assembly 120 and the fixed assembly 140 may further comprise a second sealing structure 124 and 144 providing a second seal for coupling the respective assemblies with the sample tube 110. The second sealing structure may help to ensure that atmospheric gas does not enter into the exhaust stream of the exhaust stack 104 and to ensure that exhaust gas does not escape into the atmosphere. The first and second seals may also be provided by the same sealing structure, that is, the first sealing structure 122 or 142 may be the same as the second sealing structure 124 or 144. In the exemplary embodiment shown in FIG. 5 the first sealing structure 142 and second sealing structure 144 of the fixed assembly 140 are the same component of the fixed assembly 140, as will be further described with reference to FIG. 8, whereas the first sealing structure 122 and second sealing structure 124 of the floating assembly 120 are different components of the floating assembly 120, as will be further described with reference to FIG. 7.

The floating assembly 120 may differ from the fixed assembly 140 in that the floating assembly 120 may further comprise a compressive body 126, depicted as a spring in the exemplary embodiment of FIG. 5. The compressive body 126 may help to maintain the first seals and second seals of the floating assembly 120 and fixed assembly 140 by providing a compressive force to the assemblies.

Figure 6:
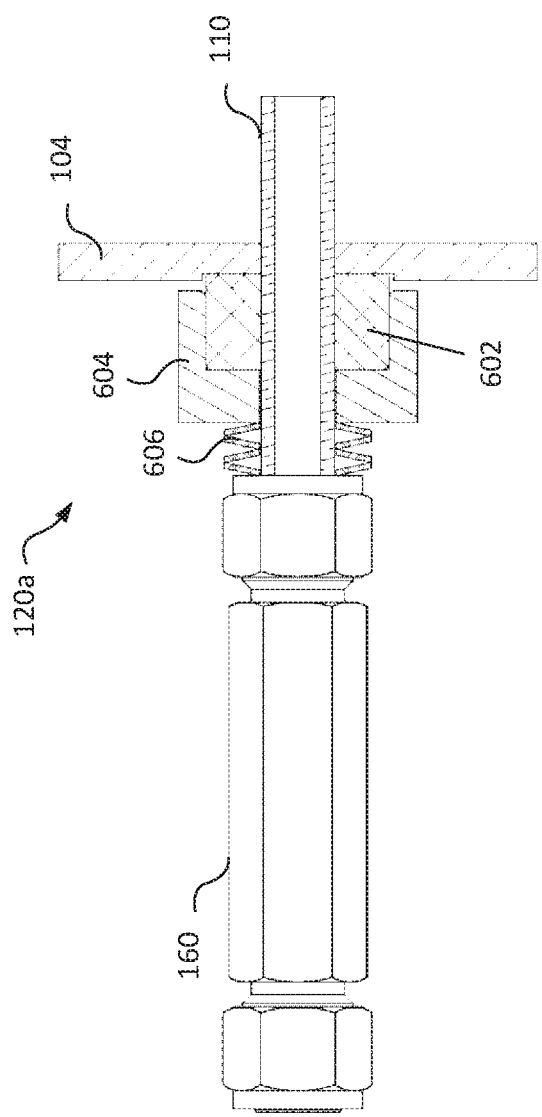
FIG. 6 shows an exemplary floating assembly that may be used in the sample port assembly.

FIG. 6 shows a cross-section of an exemplary floating assembly 120a that may be used in the sample port assembly 100. The floating assembly 120a shown in FIG. 6 is shown with reference to the exhaust stack 104 and the sample tube 110. The floating assembly 120 of this embodiment comprises packing 602, a packing gland 604, and a spring 606. The spring 606 may be disposed between the fitting 160 and the packing gland 604, thereby providing a compressive force that maintains the assembly seal against the exhaust stack through-hole even in the presence of exhaust stack vibration, misalignment of through-holes, etc.

The packing 602 in the exemplary floating structure 120a may provide the previously described first and second sealing structures 122 and 124 which may help to seal the floating assembly 120a against the exhaust through-hole and the sample tube 110. The packing 602 may be made of graphite, for example. The spring 606 may provide the compressive body 126 previously described, which may help to maintain the first and second seals. The compressive spring 606 may comprise one or more of a helical spring, disc spring, bi-metallic spring, bushing, bellow, or diaphragm.

The floating assembly 120a may slide over the end of the sample tube 110 starting with the packing 602. The packing gland 604 centers the packing 602 about the sample tube 110 and provides a mechanical stop for a distal end of the packing 602 relative to the exhaust stack 104. When a compressive force is applied to the distal end of the floating assembly 120a via the fitting 160, the spring 606 may be compressed and the force is transferred through the packing gland 604 and packing 602 to the outer surface of the exhaust stack 104.

As the packing 602 is forced into the side of the exhaust stack 104, a seal is created between the packing 602 and the surface of the exhaust stack 104 as well as between the packing 602 and the inner surface of the packing gland 604. At the same time, the compressive force also deforms the packing 602, creating a seal between the inner surface of packing 602 and the periphery of the sample tube 110. Once the desired spring pre-load is achieved in spring 606, an inner nut of the fitting 160 may be tightened securing the fitting 160 to the sample tube 110 and securing the floating assembly 120 in place against the exhaust stack 104. The spring 606 may optionally be removed under conditions where there is sufficient elasticity in the packing 602 to maintain a positive seal at all times.

Figure 7A:
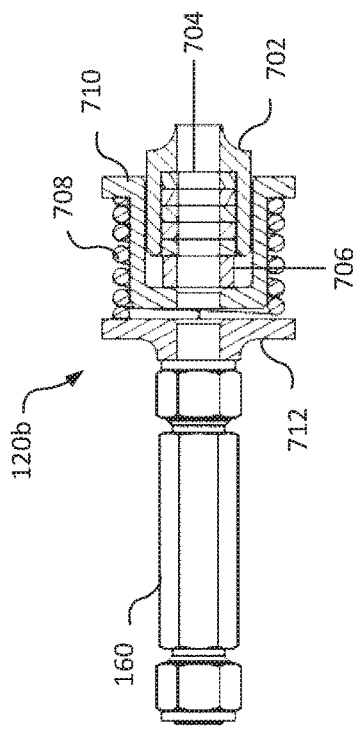
FIGS. 7A, 7B, and 7C show an alternative floating assembly that may be used in the sample port assembly.
Figure 7C:
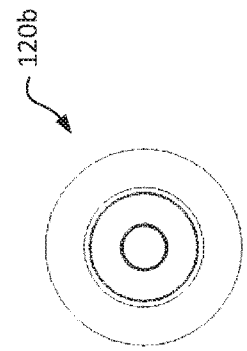
Figure 7B:
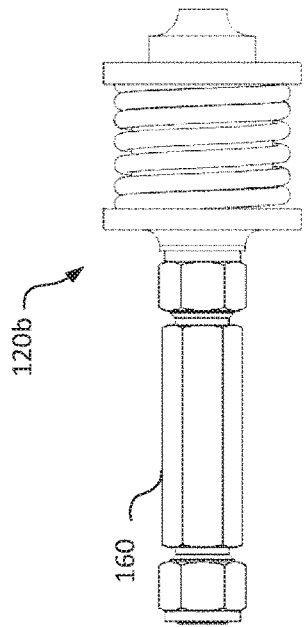

FIGS. 7A, 7B, and 7C (collectively referred to as FIG. 7) show an alternative floating assembly 120b that may be used in the sample port assembly 100. In particular, FIG. 7A shows a cross-sectional side view of the alternative floating assembly 120b, FIG. 7B shows a full side view of the alternative floating assembly 120b, and FIG. 7C shows the full front view of the alternative floating assembly 120b.

In the alternative floating assembly 120b that may be seen in FIG. 7A, the floating assembly 120b may comprise a packing gland 702 providing the first sealing structure against the exhaust stack. The packing gland 702 may have a concave surface for providing the sealed interface with the corresponding exhaust through-hole, for example exhaust through-hole 106a. Internal to the packing gland 702 may be packing 704 used for providing the second sealing structure of the floating assembly 120b against the sample tube 110. The floating assembly 120b may further comprise a packing follower 706. The packing 704 may be made of graphite, for example. The packing follower 706 may be made of stainless steel, for example.

A spring 708 may circumferentially wrap around the external surface of a spring guide 710, which in turn houses the packing gland 702, packing 704, and packing follower 706. The spring guide 710 may help to center the spring 708 about the sample tube 110 and provides a mechanical stop for one end of the spring 708. A spring stop 712 may provide a mechanical stop for the other end of the spring 708 as well as interface with the fitting 160.

The floating assembly 120b may be slid over a first end of the sample tube 110 starting with the packing gland 702. When a compressive force is applied to the spring stop 712 via the fitting 160, the spring 708 is compressed and the force is transferred through the spring guide 710, packing follower 706, packing 704, and packing gland 702 to the outer edge of the exhaust through-hole 106a in the exhaust stack 104. Changes in the compression of the spring 708 may help to compensate for the contraction and expansion and/or misalignment of the assembly during normal operation and ensures that a positive seal is maintained at all times.

As the concave surface of the packing gland 702 is forced into the exhaust through-hole 106a in the exhaust stack 104, the first seal is created between the exhaust through-hole 106a and the packing gland 702. The fitting 160 may be used to secure the floating assembly 120b in place once a desired compression of the spring 708 is achieved.

Figure 8A:
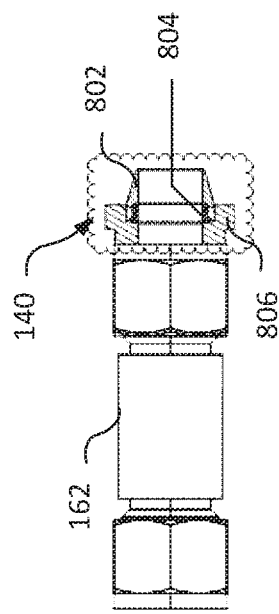
FIGS. 8A and 8B show an exemplary fixed assembly that may be used in the sample port assembly.
Figure 8B:
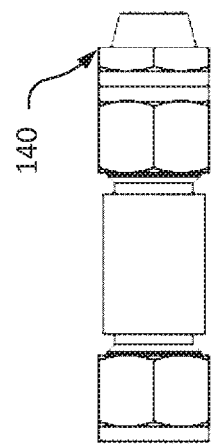

FIGS. 8A and 8B (collectively referred to as FIG. 8) show a fixed assembly that may be used in the sample port. In particular, FIG. 8A shows a cross-sectional side view of an exemplary fixed assembly 140, and FIG. 8B shows a full side view of the exemplary fixed assembly 140.

In the exemplary fixed assembly 140 as shown in FIG. 8A, the fixed assembly 140 may comprise a front ferrule 802, a back ferrule 804, and a modified nut 806. The front ferrule 802 may have a wedged surface or concave for being inserted into the corresponding exhaust through-hole, for example 106b, which provides the first sealing structure 142 described with reference to FIG. 5. The fixed assembly 140 may be slid over a second end of the sample tube 110 starting with the front ferrule 802. The inner nut of the fitting 162 may be tightened to secure the fitting 162 to the sample tube 110. At this point, the fixed assembly 140 is still free to move until a compressive force is applied between the floating assembly 120 and the fixed assembly 140. The application of a compressive force to cause the fixed assembly 140 to seal against the exhaust through-hole 106b and sample tube 110 will be further described with reference to FIG. 18, which describes a method for installing the sample port assembly. In response to the compressive force, the front ferrule 802 may be wedged into the corresponding exhaust through-hole 106b to provide the first seal of the fixed assembly 140. The front ferrule 802 in this exemplary embodiment also provides the second sealing structure 144 described with reference to FIG. 5, wherein the compressive force is transferred via the fitting 162, the modified nut 806, and the back ferrule 804 so that the front ferrule 802 swages against the sample tube 110 to provide the second seal. In an alternative scenario, instead of the ferrules swaging against the sample tube 110 in response to the compressive force, the front ferrule 802 and back ferrule 804 may be pre-swaged onto the sample tube 110 before installing the fitting 162. The front ferrule 802 and back ferrule 804 would not be free to move along the sample tube after swaging, however by pre-swaging the ferrules this may allow for a greater compression or a more controlled compression to be applied, thereby ensuring a proper seal of the fixed assembly.

In the foregoing exemplary embodiments, the packing 602 in the floating assembly 120a, the concave or wedged surface of the packing gland 702 in the floating assembly 120b, and the wedged or concave surface of the front ferrule 802 of the fixed assembly 140 are examples of first sealing structures 122 and 142 that help provide the sealed interface between the floating and fixed assemblies and the through-holes 106a and 106b of the exhaust stack 104. Similarly, the packing 602 and 704 in the respective floating assemblies 120a and 120b, and the front ferrule 802 of the fixed assembly 140 are examples of the second sealing structures 124 and 144 that help provide the second seal between the floating and fixed assemblies and the sample tube 110. A person skilled in the art will readily appreciate that several variants of sealing structures could be implemented in the floating assembly 120 and fixed assembly 140 without departing from the scope of this disclosure. To provide non-limiting examples, the concave surface of the packing gland 702 could instead be a wedged or tapered surface, and the wedged surface of the front ferrule 802 could be a concave or tapered surface. Further alternative structures for providing the first and second seals are described with reference to FIGS. 9 thru 11 and are referred to as alternative packing gland assemblies. The structures of these packing gland assemblies may be implemented for either of the floating assembly 120 and fixed assembly 140.

Figure 9:
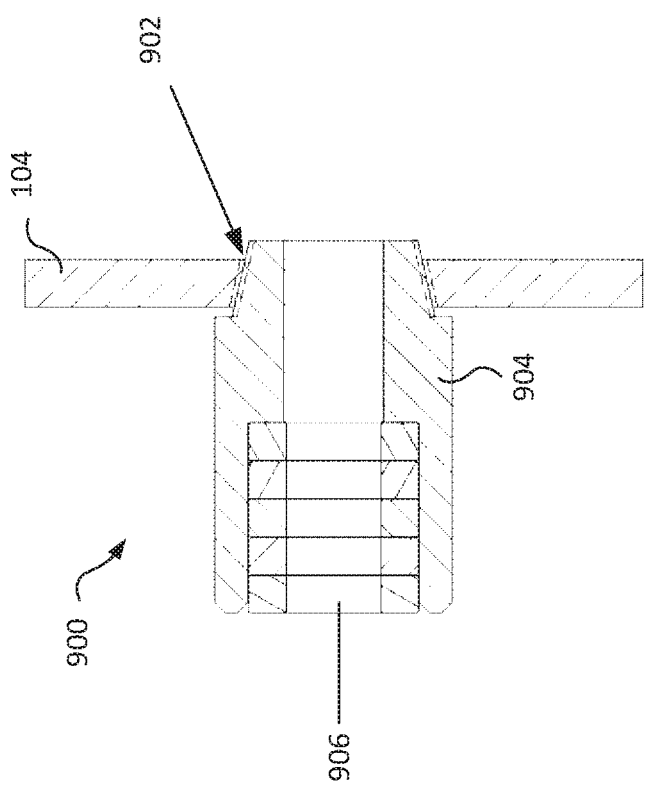
FIG. 9 shows an alternative packing gland assembly that may be used in the sample port assembly.

FIG. 9 shows an alternative packing gland assembly 900 that may be used in the sample port assembly. The packing gland assembly 900 provides for an externally threaded tapered wedge profile 902 of the packing gland 904 which may mate with internal threads in through-holes 106a or 106b in the exhaust stack 104. With this implementation, the packing gland 904 screws into the exhaust stack 104 and the threads provide the seal between the corresponding through-hole 106a and 106b in the exhaust stack 104. The packing 906 may provide the second sealing structure between the packing gland assembly 900 and the sample tube.

Figure 10:
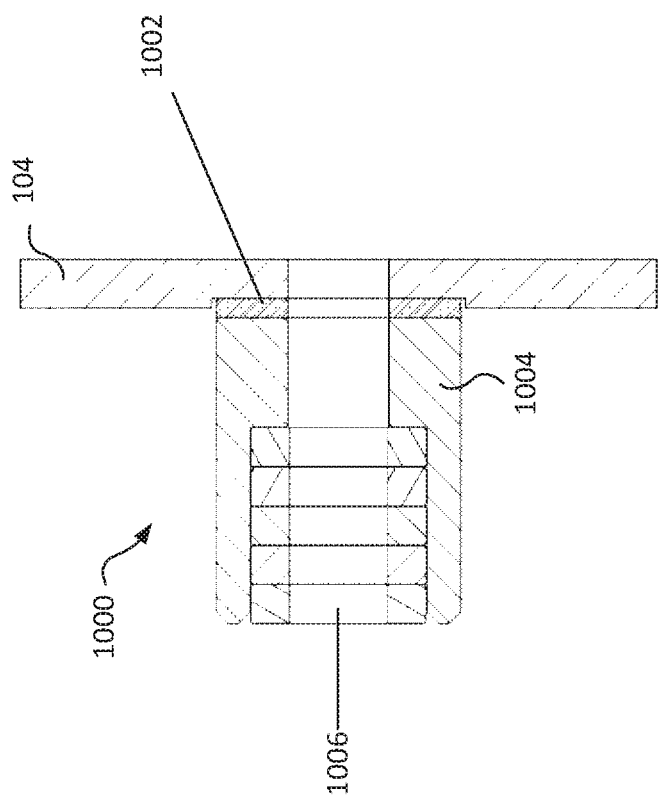
FIG. 10 shows an alternative packing gland assembly that may be used in the sample port assembly.

FIG. 10 shows an alternative packing gland assembly 1000 that may be used in the sample port assembly. The packing gland assembly 1000 provides for a flat profile of packing gland 1004 to interface with the exhaust through-hole and provide a seal there-between. With this implementation, the areas immediately surrounding the through-holes in exhaust stack 104 may be spot faced or counter-bored and a flat gasket 1002 may be inserted between the flat profile of the packing gland assembly 1000 and the spot faced or counter-bored surface of the exhaust stack 104 to provide the required seal. The packing 1006 may provide the second sealing structure between the packing gland assembly 1000 and the sample tube.

Figure 11:
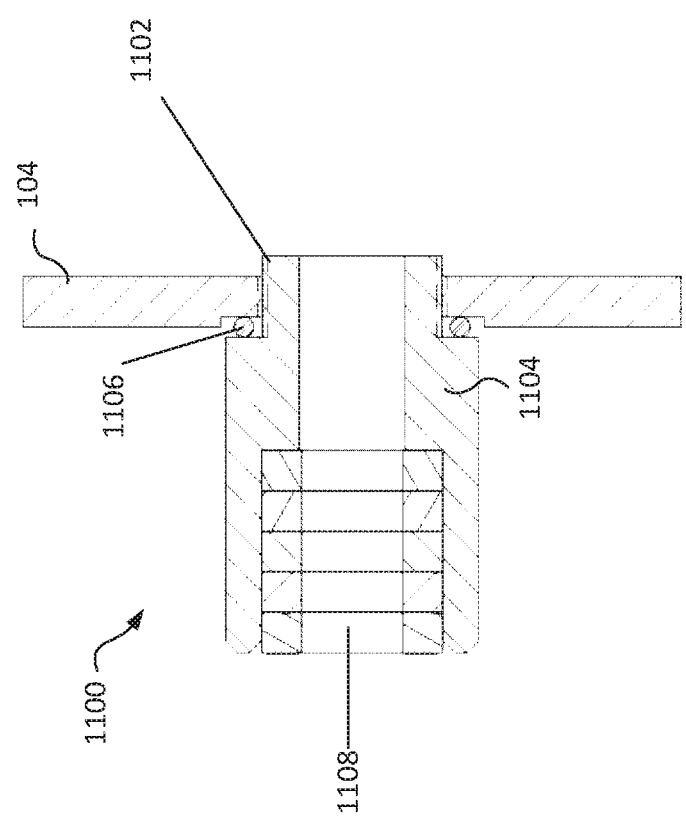
FIG. 11 shows an alternative packing gland assembly that may be used in the sample port assembly.

FIG. 11 shows an alternative packing gland assembly 1100 that may be used in the sample port assembly. The packing gland assembly 1100 provides for the use of an externally threaded parallel profile 1102 of the packing gland 1104 and an O-ring gasket 1106, or flat gasket or other sealing or similar seal, to interface with the exhaust through-hole and provide a seal. With this implementation, the areas immediately surrounding the through-holes in the exhaust stack 104 are spot faced or counter-bored and the O-ring 1106 is inserted between the flat profile of the packing gland assembly 1100 and the spot faced or counter-bored surface of the exhaust stack 104 to provide the required seal. The packing 1108 may provide the second sealing structure between the packing gland assembly 1100 and the sample tube.

A yet further option (not shown), provides for a saddle profile that fits the contour of the exhaust stack 104. A contoured flat gasket may be used to provide the seal between the saddle and the exhaust stack 104.

A person skilled in the art will readily appreciate that the configurations and sealing structures described above are exemplary in nature and that many other sealing structures could be used to provide the seal between floating and/or fixed assemblies 120 and 140 with the sample tube and the corresponding through-hole in the exhaust stack 104 without departing from the scope of this disclosure.

Figure 12:
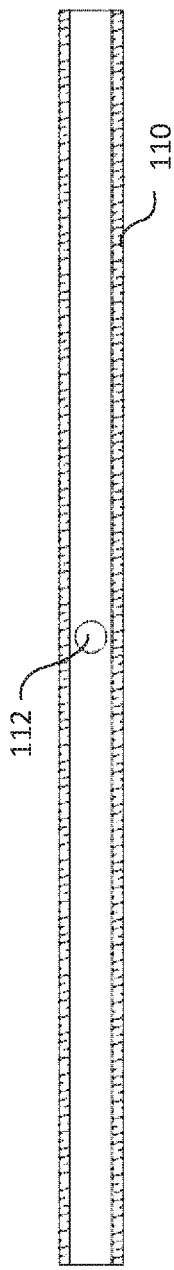
FIG. 12 shows a cross-section of a sample tube that may be used in the sample port assembly.

FIG. 12 shows a cross-section of a sample tube 110 that may be used in the sample port assembly 100. As described with reference to FIG. 5, the sample tube 110 may comprise a sample hole 112 along the outer surface of the sample tube 110 and configured to receive the exhaust gas or fluid to be sampled. The orientation of the sample hole 112 relative to the exhaust flow and the positioning of each hole along the along the length of the sample tube 110a may vary as required by the sample technique.

Figure 13:
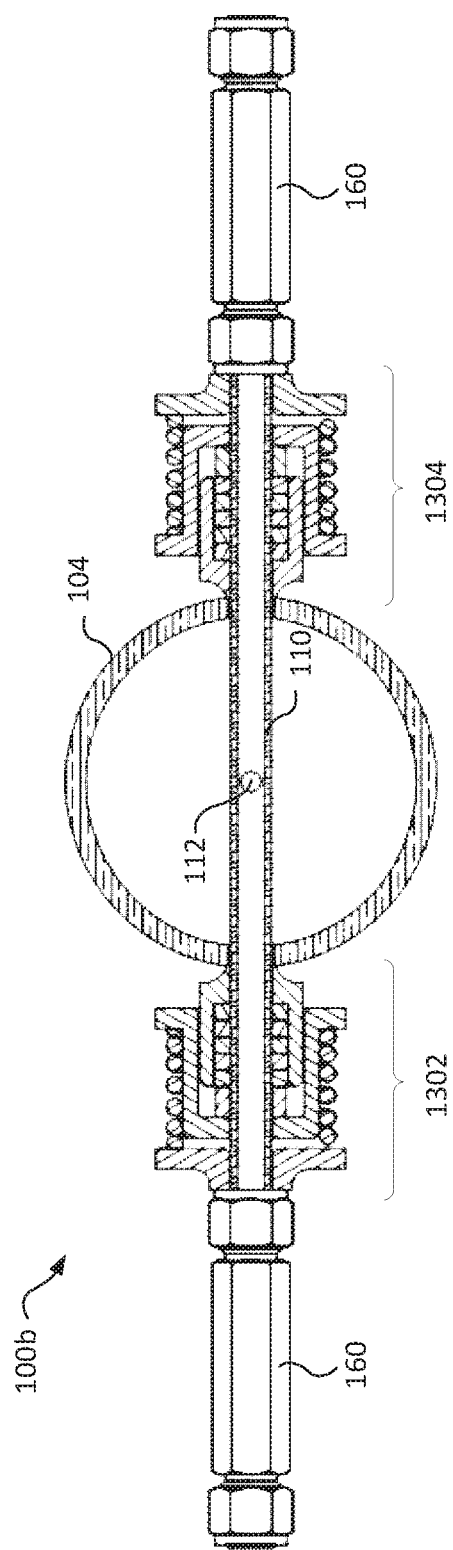
FIG. 13 shows a cross-sectional plan view of an alternative sample port assembly installed on the exhaust stack.

FIG. 13 shows a cross-sectional plan view of an alternative sample port assembly 100b installed on the exhaust stack 104. The sample port assembly 100b corresponds to the sample port configuration of having both the first and second assembly being floating assemblies 120, shown as floating assemblies 1302 and 1304 in FIG. 13. The first and second floating assembly may be the same or different, and are shown as being the same in FIG. 13. The first and second floating assemblies 1302 and 1304 may be any of the floating assemblies as previously described, though are exemplary shown as floating assembly 120b described with reference to FIG. 7. The fittings 160 on distal ends of the respective floating assemblies 120 may also be the same or different, though are shown as being the same in FIG. 13.

The sample port assembly 100b with this arrangement of using two floating assemblies 120 may provide for additional flexibility and tolerance to compensate for the contraction and expansion and/or misalignment of the assembly during normal operation and to ensure that a positive seal is maintained at all times, as compared to just using a single floating assembly 120 and a fixed assembly 140. Due to the increased flexibility, the use of two floating assemblies 120 may require compensation for spring deflection when positioning the sample hole 112 in the exhaust stream.

Figure 14:
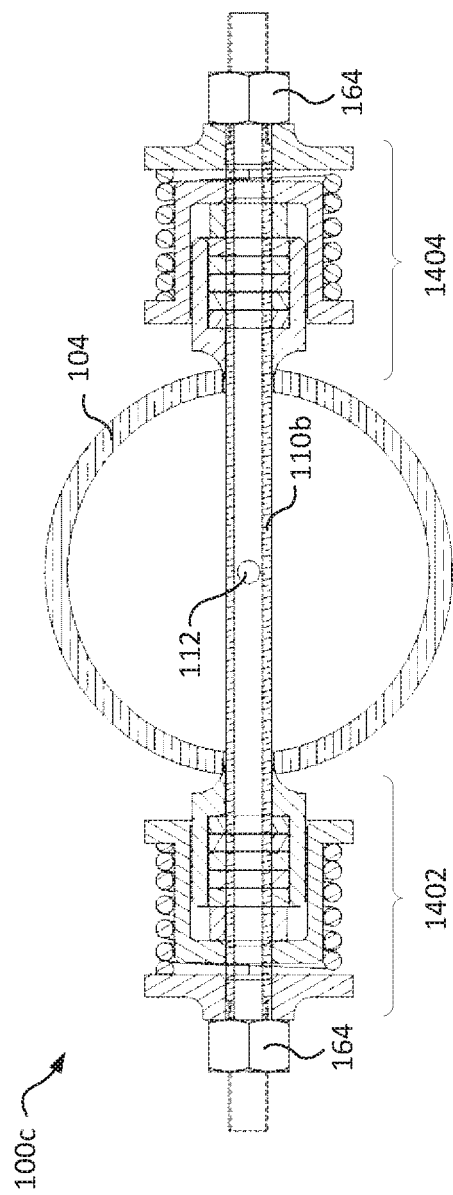
FIG. 14 shows a cross-sectional plan view of an alternative sample port assembly installed on the exhaust stack.

FIG. 14 shows a cross-sectional plan view of an alternative sample port assembly 100c installed on the exhaust stack 104. The sample port 100c is similar to the sample port 100b shown in FIG. 13 in that it comprises two floating assemblies 1402 and 1404, however a threaded sample tube 110b is shown as being used instead of the traditional sample tube 110, and instead of fittings 160 or 162 that have been previously described as swaged fittings, threaded nuts 164 are used to secure against the sample tube and hold the floating assemblies 120 in place along an axial location of the threaded sample tube 110b. Thus, in this exemplary embodiment the position of the threaded sample tube 110b, the sampling location, and spring or compressive body pre-load may be altered by adjusting the relative positions of the threaded nuts 164. This sample port assembly 100c may help to facilitate the removal of the sample port assembly for inspection and allows for future adjustment of the spring pre-load to compensate for changes in the spring force over time. While fittings are not depicted in FIG. 14 to allow a connection to sampling equipment as will be described with reference to FIG. 15, it will be readily apparent to a person skilled in the art how a threaded fitting or the like may be implemented to allow for such a connection.

The sample port assemblies 100a-100c described herein are exemplary in nature and are shown to depict possible configurations and variations of the sample port assembly 100. A person skilled in the art will readily appreciate that sample port assemblies having different configurations may be used without departing from the scope of this disclosure.

Figure 15:
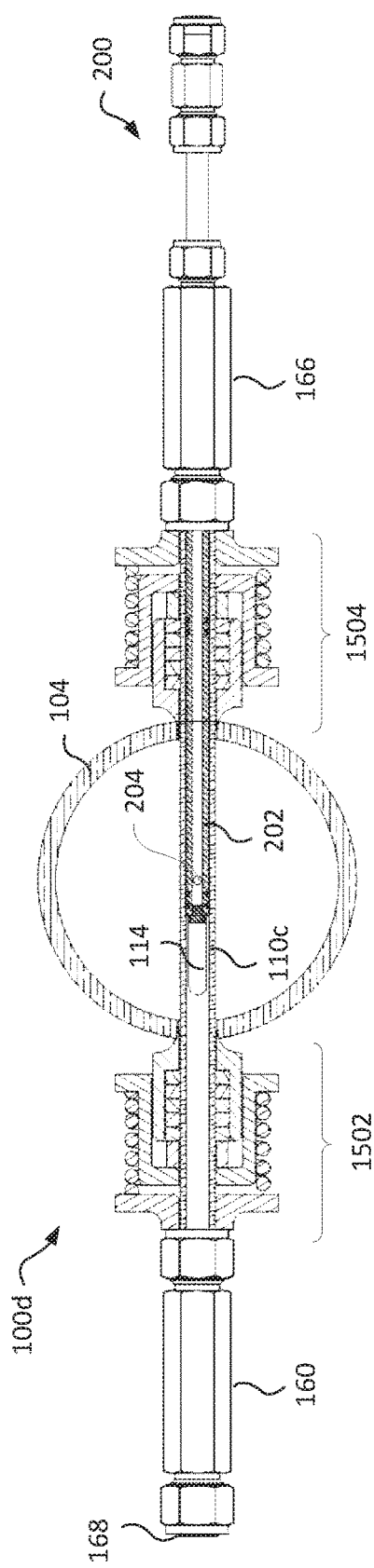
FIG. 15 shows a cross-sectional plan view of a system for sampling a fluid comprising the sample port assembly.

FIG. 15 shows a cross-sectional plan view of a system for sampling a fluid comprising the sample port assembly 100d. The sample port assembly 100d comprises two floating assemblies 1502 and 1504 similar to sample port assembly 100b, however an alternative sample tube 110c is shown which may comprise a sample slot 114 as opposed to a sample hole 112. A sample probe 200 comprising a sample probe tube 202 with a sample probe hole 204 thereon may be inserted into one of the floating assemblies as shown. This configuration may allow for stack traversing, wherein the sample probe hole 204 may be moved over the sample slot 114 to receive the sample at different radial positions in the exhaust stack 104. A fitting 166 may be provided adjacent to the floating assembly 120 for which the sample probe 200 is inserted through. The fitting 166 may be similar to the fittings 160 or 162 such that an inner nut may allow for the fitting 166 to be tightened against the sample tube 110c, however the fitting 166 may include an outer nut or an outer connection without a cap 168 and which allows for the fitting 166 to provide a seal and be coupled with the sample probe 200. For example, the outer nut of fitting 166 may comprise a ductile ferrule, and when the sample probe 200 is in the desired position the outer nut of fitting 166 may be tightened against the sample probe 200 to provide a seal and secure the fitting 166 to the sample probe. The use of a ductile ferrule in fitting 166 may facilitate repositioning of the sample probe 200, though this represents just one embodiment and the scope of the invention is not limited to such.

While the alternative sample tube 110c and the sample probe 200 are shown in FIG. 15 as being used with the sample port assembly 100d, which comprises two floating assemblies 120, it will be appreciated by a person skilled in the art that these elements could be used with any of the sample ports 100a-c.

Figure 16:
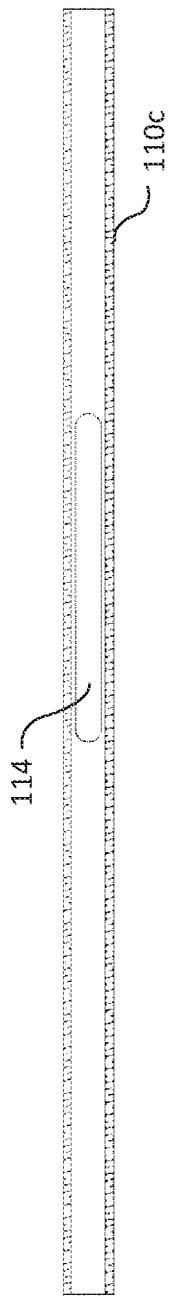
FIG. 16 shows a cross-section of an alternative sample tube that may be used in the sample port assembly.

FIG. 16 shows a cross-section of the sample tube 110c that may be used in the sample port assembly 100. As described with reference to FIG. 15, the sample tube 110c may comprise a sample slot 114 along the outer surface of the sample tube 110c and configured to receive the exhaust gas or fluid to be sampled. Alternatively, instead of or in addition to a sample slot 114, a plurality of sample holes (not shown) may be provided along the length of the sample tube at different locations. Such a configuration may similarly allow for stack traversing, and in order to align the sample probe hole 204 with respective sample holes of the plurality of sample holes, an external indication of position may be required.

Figure 17:
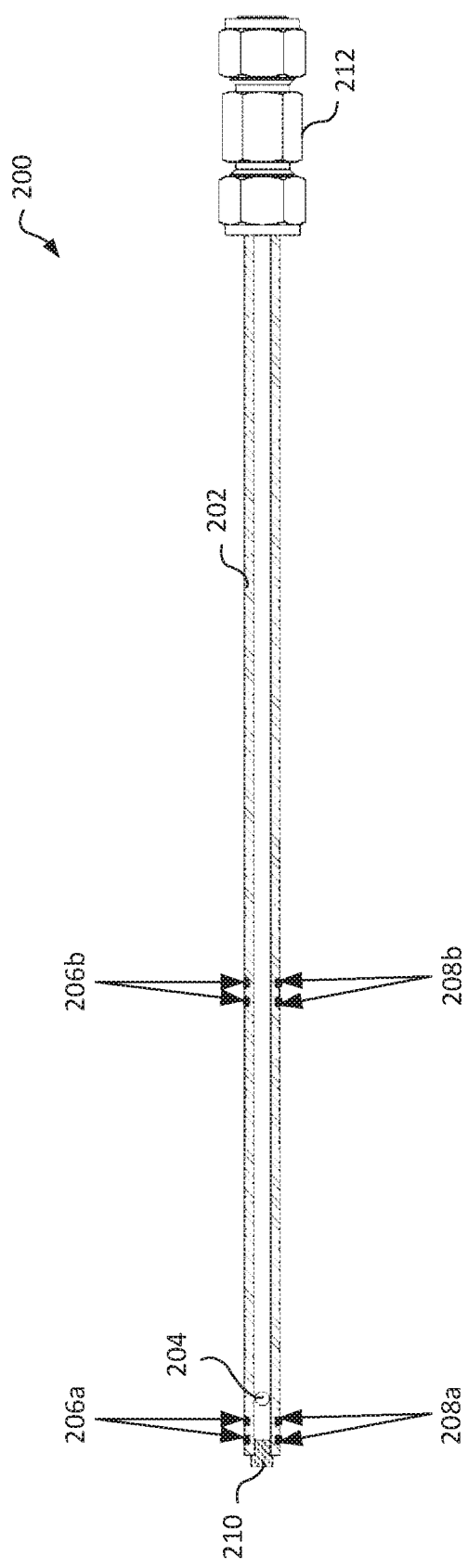
FIG. 17 shows a cross-section of a sample probe that may be used in the system for sampling a fluid.

FIG. 17 shows a cross-section of a sample probe 200 that may be used in the system for sampling a fluid. As described with reference to FIG. 15, the sample probe 200 may comprise a sample probe tube 202 and a sample probe hole 204 located thereon which can be moved relative to the sample slot 114 (or to different sample holes) to collect fluid samples a different positions with the conduit. The sample probe hole 204 may be perpendicular to the sample probe tube's outer surface. The sample probe 200 may further comprise rings 206a and 206b that slide over radial grooves 208a and 208b on the periphery of the sample probe tube 202, and which may provide a primary high temperature seal between the sample probe tube 202 and the inner surface of the sample tube 110c. The sample probe 200 may further comprise a plug 210, which may help to ensure that the sample may only be drawn through the sample probe hole 204. A sample probe fitting 212 may be provided at an end of the sample probe 200 opposite the sample plug 210, which may be used to create a seal to prevent exhaust gases from leaking to the atmosphere. The sample probe fitting 212 may be include but not be limited to: swaged tube fittings, tapered thread fittings, or the like, and may correspond to the fitting 160, 162, or 166 on the sample port assembly 100 with which the sample probe fitting 212 mates.

Starting with the plug 210, the sample probe 200 may slide into one end of the sample port assembly 100, for example through the floating assembly 120 as shown in FIG. 15 via the fitting 166. The angular position of the sample probe hole 204 may be positioned so that it is aligned with the sample slot 114 in the sample tube 110c. The location of the sample probe 200 may be adjusted to the desired location, that is, the sample probe hole 204 adjusted to be positioned over the desired location along the sample slot 114. Once in the correct position, the outer nut of the fitting 166 may be tightened and secured to the sample probe tube 202 as previously described with reference to FIG. 15.

Figure 18:
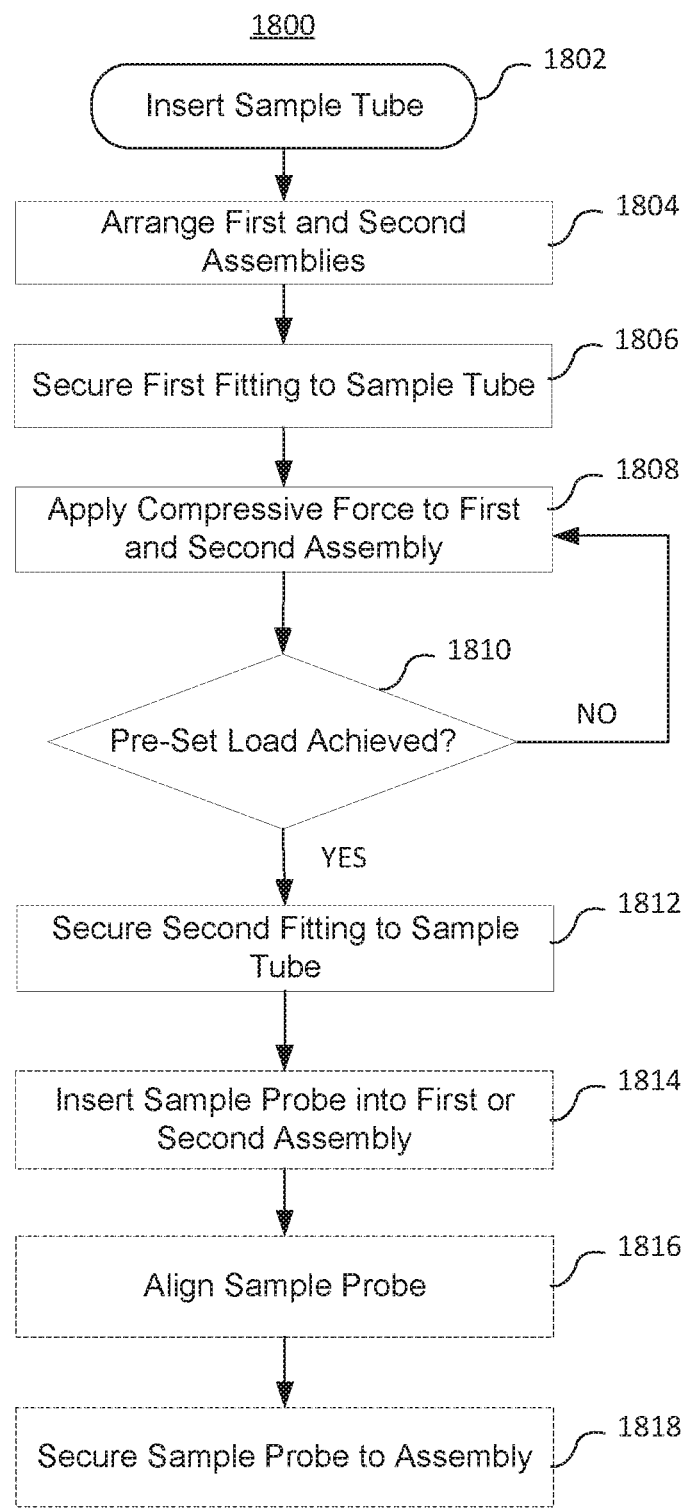
FIG. 18 shows a method for installing the sample port assembly.

FIG. 18 shows a method 1800 for installing the sample port assembly 100. The sample tube (for example sample tube 110) may be inserted into the conduit such as an exhaust stack (for example through pre-made exhaust through-holes 106a and 106b) or other conduit from which the sample is to be received from (1802). The sample tube may be inserted substantially perpendicular to the direction of fluid flow, with the sample hole 112 or sample slot 114 positioned accordingly for receiving the sample of fluid. The first and second assemblies, as well as fittings interfacing with the first and second assemblies, may be slid over respective ends of the sample tube and positioned outside of the exhaust stack (1804). Prior to sliding the first and second assemblies onto the sample tube, or after one of the assemblies has been slid over the tube but prior to sliding the second of the assemblies over the tube, the sample tube 110 may be cut to an appropriate length to facilitate the assembly, though it is not necessary.

A first fitting may be secured with the sample tube 110 (1806). For example, if a fixed assembly (for example fixed assembly 140) is used as the first assembly and is slid over an end of the sample tube 110 until the sample tube 110 contacts the fitting 162, the fitting 162 may be tightened to secure against the sample tube 110 and prevent movement of the fixed assembly 140 along the sample tube 110 past the fitting 162. A compressive force may be applied to the first and second assemblies (1808). The compressive force causes the first and second sealing structures of the first and second assemblies to provide a seal against the respective exhaust through-holes 106a and 106b, as well as sample tube 110. For example, if the second assembly is the floating assembly 120, the first sealing structure may be the packing gland 702 and the second sealing structure may be the packing 704 as shown in FIG. 7. If the first assembly is the fixed assembly 140, the first and second sealing structure may be the front ferrule 802 as shown in FIG. 8. A threaded tube, for example, may be used to apply the compressive force for assembly of the sample port assembly 100, though numerous techniques for applying a compressive force to the first and second assemblies may be implemented without departing from the scope of this disclosure.

At least one of the first and second assemblies comprises a compressive body. The compressive force may continue to be applied until a pre-set load in the compressive body is achieved. A determination is made if the pre-set load is achieved (1810), for example if a spring 708 is used as a compressive body in the floating assembly 120 this determination may be made based on a displacement (contraction) of the spring 708. The pre-set load may correspond to a compressive load at which the first and second seals of the first and second assemblies provide a sufficient seal to the conduit. A sufficient seal may be deemed such that the first and second seals of the first and second assemblies are maintained even under worst-case conditions for differential expansion/contraction of the exhaust stack 104 and sample tube 110. For example, under start-up conditions, the sample tube 110 may warm up and expand faster than the exhaust stack 104, which would in turn reduce the compressive force applied to the seals. The pre-set load may correspond to a compressive load that provides this tolerance and ensures that the first and second seals are maintained.

If the pre-set load has not been achieved (NO at 1810), the compressive force continues to be applied (1808). If the pre-set load has been achieved (YES at 1810), the second fitting is secured with the sample tube 110 (1812), for example by tightening the inner nut of the fitting 160, thereby securing the second assembly between the fitting 160 and the exhaust stack 104. The compressive force may then be removed. A cap or plug may optionally be placed on the fittings connected to both the first and second assemblies if sampling is not taking place, or only on one of the fittings if sampling is taking place and an equipment connection has been made to one of the fittings.

Optionally, it may be desirable to perform sampling via stack traversing, and the sample tube 110 may comprise a corresponding sample slot 114 to correspond to this functionality (as shown in the sample tube 110c of FIG. 16 for example). As described with reference to FIGS. 15 thru 17, a sample probe (for example sample probe 200) may be inserted into the sample port assembly 100 through one of the first or second assemblies (1814). The sample probe 200 may be appropriately aligned (1816), for example by aligning the sample probe hole 202 over the desired location of the sample tube slot 114. The fitting of the assembly through which the sample probe 200 has been inserted may be tightened against the sample probe tube to secure the sample probe and provide a seal (1818), as described for example with regards to FIG. 15.

The method for installing the sample port assembly 100 as described above is non-limiting and exemplary in nature. A person skilled in the art will readily appreciate that the sample port assembly 100 may have numerous different configurations as described herein, and accordingly the method of assembly may vary slightly without departing from the scope of this disclosure. In another embodiment, for example, the sample port assembly 100 may comprise two floating assemblies such as the sample port assembly 100b shown in FIG. 13. There may be a need to compensate for spring deflection when securing the two floating assemblies in place to provide accurate positioning of the sample hole of the sample tube in the exhaust stream. The method 1800 may secure the first and second fittings to the sample tube 110 after the pre-set load has been achieved (YES at 1810).

It would be appreciated by one of ordinary skill in the art that the system and components shown in FIGS. 3-18 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

Although certain components and steps have been described, it is contemplated that individually described components, as well as steps, may be combined together into fewer components or steps or the steps may be performed sequentially, non-sequentially or concurrently. Further, although described above as occurring in a particular order, one of ordinary skill in the art having regard to the current teachings will appreciate that the particular order of certain steps relative to other steps may be changed. Similarly, individual components or steps may be provided by a plurality of components or steps. One of ordinary skill in the art having regard to the current teachings will appreciate that the system and method described herein may be provided by various combinations of hardware, other than the specific implementations described herein as illustrative examples. Numerous additional variations on the methods and apparatus of the various embodiments described above will be apparent to those skilled in the art in view of the above description. Such variations are to be considered within the scope of the present invention.

The invention claimed is:

1. A weldless sample port assembly for extracting a sample from a fluid carried by a conduit, the weldless sample port assembly comprising:
   a sample tube configured to be inserted through two holes in the conduit, the sample tube arranged perpendicular to a direction of fluid flow and configured to receive a sample of fluid;
   a first assembly coupled to the sample tube at a first end of the sample tube outside of the conduit, the first assembly for providing a compressively sealed interface with a first hole of the two holes in the conduit, the first assembly being a first floating assembly comprising a first compressive body; and
   a second assembly coupled to the sample tube at a second end of the sample tube outside of the conduit, the second assembly for providing a compressively sealed interface with a second hole of the two holes in the conduit,
   wherein, when the weldless sample port assembly is installed against the conduit, the first compressive body maintains the compressively sealed interfaces of the first and second assemblies with the first and second holes.

2. The weldless sample port assembly of claim 1, wherein the second assembly is a fixed assembly.

3. The weldless sample port assembly of claim 1, wherein the first compressive body comprises any one or more of a spring, a bushing, a bellow, and a diaphragm.

4. The weldless sample port assembly of claim 3, wherein the floating assembly further comprises a packing gland assembly, the first compressive body comprises the spring and the spring is circumferentially disposed around an external surface of the packing gland assembly.

5. The weldless sample port assembly claim 2, wherein each of the floating assembly and the fixed assembly comprise a first sealing structure providing a first seal between the respective floating assembly and fixed assembly and the respective first hole and second hole, and a second sealing structure providing a second seal between the respective floating assembly and fixed assembly and the sample tube.

6. The weldless sample port assembly of claim 5, wherein the first sealing structure of the floating assembly comprises any one or more of: packing, a concave packing gland, a tapered packing gland, a threaded packing gland, a flat packing gland, and a packing gland with a saddle profile.

7. The weldless sample port assembly of claim 5, wherein the first sealing structure of the fixed assembly comprises any one or more of: a ferrule, packing, a concave packing gland, a tapered packing gland, a threaded packing gland, a flat packing gland, and a packing gland with a saddle profile.

8. The weldless sample port assembly of claim 1, wherein the second assembly is a second floating assembly comprising a second compressive body.

9. The weldless sample port assembly of claim 8, wherein the first and second compressive bodies respectively comprise any one or more of a spring, a bushing, a bellow, and a diaphragm.

10. The weldless sample port assembly of claim 9, wherein at least one of the first and second floating assemblies further comprise a packing gland assembly, a corresponding of the first and second compressive body comprises the spring, and the spring is circumferentially disposed around an external surface of the packing gland assembly.

11. The weldless sample port assembly of claim 8, wherein each of the first and second floating assemblies comprise a first sealing structure providing a first seal between the respective floating assembly and the respective first hole and second hole, and a second sealing structure providing a second seal between the respective floating assembly and the sample tube.

12. The weldless sample port assembly of claim 11, wherein the first sealing structure comprises any one or more of: packing, a concave packing gland, a tapered packing gland, a threaded packing gland, a flat packing gland, and a packing gland with a saddle profile.

13. The weldless sample port assembly of claim 1 further comprising a first fitting and a second fitting interfacing with respective of the first assembly and the second assembly at a distal end thereof with respect to the conduit, the first and second fittings configured to be secured with the sample tube.

14. The weldless sample port assembly of claim 13, wherein the first fitting and the second fitting are configured to receive one or more of a sample measurement device and a cap.

15. The weldless sample port assembly of claim 1, wherein the sample tube comprises one of: a hole, a plurality of holes, or a slot, configured to receive the sample of fluid there through.

16. The weldless sample port assembly of claim 1, wherein the sample tube is further configured to receive a sample probe inserted there through, the sample probe comprising a sample probe tube and a sample probe hole at an end thereof for receiving the sample of fluid.

17. The weldless sample port assembly of claim 1 wherein the fluid is one or both of a gas and a liquid.

* * * * *